United States Patent [19]

Wilson

[11] Patent Number: 5,437,675
[45] Date of Patent: Aug. 1, 1995

[54] POLYGONAL BONE PUNCH

[76] Inventor: Franklin D. Wilson, 34 TwinShore Ct., Carmel, Ind. 46033

[21] Appl. No.: 75,983

[22] Filed: Jun. 11, 1993

[51] Int. Cl.⁶ .............................................. A61B 17/16
[52] U.S. Cl. ...................................... 606/80; 606/185; 30/358
[58] Field of Search .................. 606/79, 80, 83, 84, 606/167, 185; 30/366, 358; D24/146

[56] References Cited

U.S. PATENT DOCUMENTS

| | | | |
|---|---|---|---|
| 1,934,962 | 11/1933 | Barry | 606/84 |
| 2,250,434 | 7/1941 | Dugaw | 30/358 |
| 3,060,782 | 10/1962 | Burgess | 30/358 |
| 3,143,026 | 8/1964 | Akerson | 83/686 |
| 4,944,744 | 7/1990 | Ray | 606/84 |
| 5,139,499 | 8/1992 | Small et al. | 606/73 |
| 5,139,520 | 8/1992 | Rosenberg | 623/13 |
| 5,163,940 | 11/1992 | Bourque | 606/96 |

FOREIGN PATENT DOCUMENTS 2187990  9/1987  United Kingdom ............. 606/84

OTHER PUBLICATIONS

The Paramax ™ ACL Guide System Surgical Technique, a brochure of Linvatec Corporation, 1992.
Innovation & Documentation, a catalog of Instrument Makar, Inc., pp. 3–5, 1993.

Primary Examiner—Tamara L. Graysay
Attorney, Agent, or Firm—Douglas E. Denninger; David A. Warmbold

[57] ABSTRACT

A bone punch for altering the cross-section of a tunnel formed in a bone, the punch having a punch body with a distal region, a proximal region, and a plurality of planar guide faces extending between the distal and proximal regions to define a polygon in cross-section. The distal region terminates in a narrowed leading end to facilitate entry into the pre-drilled tunnel. A shaft is connected to the proximal region to transmit a force to drive the punch body into the bone tunnel to alter the cross-section shape of the bone tunnel to match the polygonal cross-section of the punch body.

14 Claims, 2 Drawing Sheets

POLYGONAL BONE PUNCH

FIELD OF THE INVENTION

This invention relates to a bone punch for compacting a bone tunnel and more particularly to a punch which converts a round hole drilled in a bone into a tunnel having a polygonal cross section.

BACKGROUND OF THE INVENTION

There are a several types of surgical procedures in which a soft tissue graft is secured within a tunnel formed in a bone. A number of surgeons reconstruct a damaged cruciate ligament using a patellar tendon graft. The disclosures of U.S. Pat. Nos. 5,139,520 (Rosenberg), 5,139,499, (Small, et al.), and 5,163,940 (Bourque) are incorporated herein by reference.

After harvesting, the patellar tendon graft comprises a length of soft tissue secured at either end to a bone plug. The bone plugs typically have a rectangular or trapezoidal cross-section and then are carved into a round shape to fit into circular holes drilled into the tibia and femur. Alternatively, larger round holes are drilled to accommodate the non-round shape of the bone plugs.

Other surgeons utilize round dilators of increasingly larger diameters to form a round tunnel in a femur by compaction. The bone plugs are shaped into a matching round cross-section, and are sized using a bar having holes formed therein of different indicated diameters, one of which is selected by the surgeon as corresponding to the hole formed in the bone.

Bone plugs typically are secured within a bone tunnel using an interference screw. Difficulty may be encountered during the insertion of an interference screw between the bone plug and the wall of the bone tunnel. The screw sometimes converges or diverges from its intended path which may weaken its anchoring ability and may even fracture the bone plug. A screw guide sold under the trademark TRAILBLAZER, available from Acufex Microsurgical, Inc., Mansfield, Mass., is a circular punch having a conical distal tip which is inserted between the bone plug and the tunnel wall prior to inserting an interference screw to encourage proper placement of the screw.

Another conventional device utilizes a round punch with a semi-circular offset that is inserted into the bone tunnel prior to inserting the bone plug. The round offset forms a curved groove which may assist subsequent screw placement. Another goal of this device is to minimize rotation of the bone plug during screw insertion.

The above-described techniques still require the extra step of shaping the harvested bone plug into a circular cross-section. Further, multiple instruments must be inserted and removed to provide a separate channel for an interference screw.

If unshaped, the bone plugs do not conform to the cross-section of the tunnel. The spaces between the plug and the tunnel may retard bone fusion and healing.

SUMMARY OF THE INVENTION

Therefore, it is an object of the present invention to provide a polygonal bone punch having a number of flat faces corresponding to the shape of a harvested bone plug.

It is a further object of this invention to provide such a bone punch which minimizes rotation of a polygonal patellar graft.

Yet another object of this invention is to provide such a bone punch which forms a tunnel having a larger cross-section which increases bone surface contact with a bone plug and promotes bone ingrowth and healing.

A still further object of this invention is to provide such a bone graft which maintains proper positioning of the tendinous portion of a patellar tendon graft during and after fixation.

Yet another object of this invention is to provide a polygonal bone punch having an offset which minimizes divergence and convergence of interference screws, and minimizes any possibility of fracturing a patellar bone block during screw insertion.

This invention features a bone punch for altering the cross-section of a tunnel formed in a bone, the punch having a punch body with a distal region, a proximal region, and a plurality of planar guide faces extending between the distal and proximal regions to define a polygon in cross-section. The distal region terminates in a narrowed leading end to facilitate entry into the pre-drilled tunnel. A shaft is connected to the proximal region to transmit a force to drive the punch body into the bone tunnel to alter the cross-section shape of the bone tunnel to match the polygonal cross-section of the punch body.

In one embodiment, the punch body has a longitudinal axis and the guide faces extend substantially parallel to the longitudinal axis. The leading end of the distal region defines at least one tapered ram face for engaging a corresponding area of the bone tunnel to compact the bone. The punch further includes a ridge extending along one of the guide faces for providing a channel for an interference screw. A distal portion of the ridge defines an upper ram surface for compacting the bone to provide the screw channel. The polygonal cross-section of the punch body is rectangular, and at least one of the guide faces and the ridge carries markings to indicate depth of insertion of the punch body into the bone tunnel, such as into a femoral tunnel.

This invention also features a combination of such a bone punch and a sizing block which defines at least one sizing opening with a cross-sectional shape substantially the same as the polygonal shape of the bone punch. The sizing opening has dimensions at least slightly smaller than the cross-section of the bone punch. Preferably, the sizing block defines characters indicating a width of a bone plug to be matched with the sizing opening.

This invention further features a method of reconstructing a cruciate ligament, including forming a tunnel in a femur to have a circular cross-section. A replacement ligament is provided with a bone plug attached to one end, the bone plug having a polygonal cross-section. A bone punch as described above is provided which also has a polygonal cross-section. The distal region of the punch body is placed at the end of the femoral tunnel and force is applied to the shaft to drive the punch body into the femoral tunnel to alter the cross-sectional shape of the bone tunnel to match the polygonal cross-section of the bone plug and the punch body. Preferably, the punch body is selected to have cross-sectional dimensions at least slightly larger than those of the bone plug.

BRIEF DESCRIPTION OF THE DRAWINGS

Other objects, features and advantages will occur from the following description of a preferred embodiment and the accompanying drawings, in which.

DETAILED DESCRIPTION OF THE PREFERRED EMBODIMENT

Figure 1:
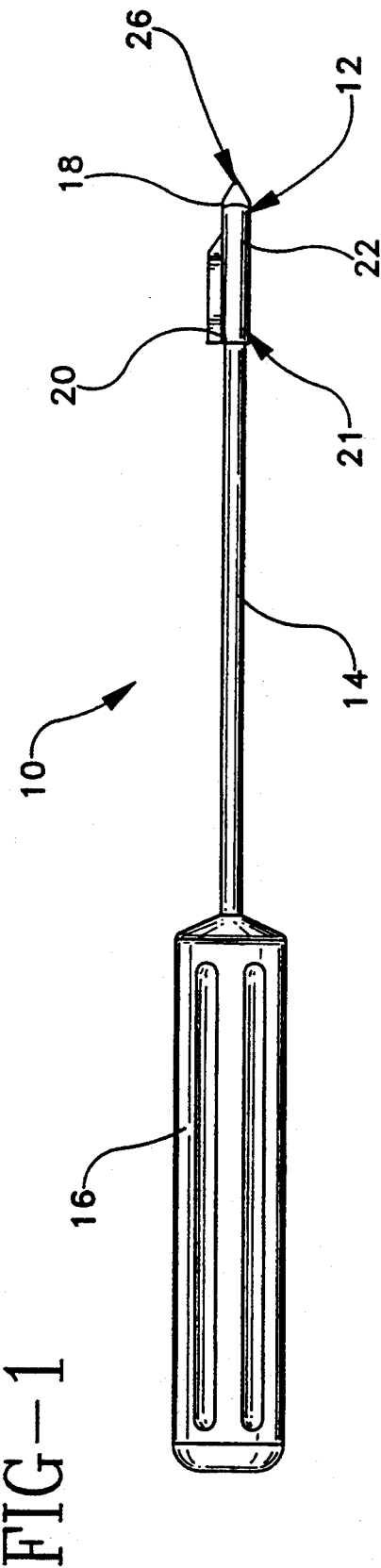
FIG. 1 is a side elevational view of a bone punch according to the present invention.
Figure 3:
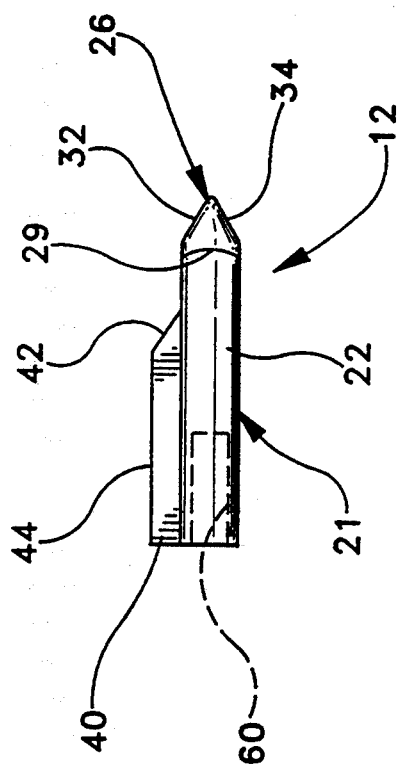
FIG. 3 is a side elevational view of the punch body of FIG. 1.
Figure 2:
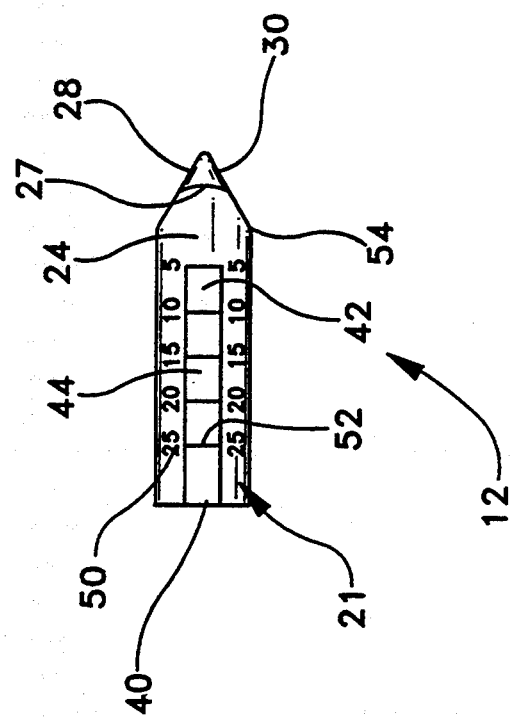
FIG. 2 is a top plan view of the punch body of FIG. 1.

A bone punch 10, FIGS. 1-3, has a punch body 12, a shaft 14, and a handle 16. The punch body 12 has a distal region 18, a proximal region 20, and a plurality of guide faces 21, of which a side guide face 22 is shown in FIGS. 1 and 3, and a top guide face 24 is shown in FIG. 2. The punch body 12 has a longitudinal axis aligned with the shaft 14 and the handle 16, and the guide faces 21 extend substantially parallel to the longitudinal axis.

In this construction, the punch body 12 defines a rectangle in cross-section, which is particularly suitable for bone plugs having a rectangular or sightly trapezoidal cross-section. Other polygonal cross-sections can be utilized to match the desired cross-section of the bone plug and the desired shape of the bone tunnel into which the bone plug is to be inserted.

The distal region 18 includes a conical ram face 26 which include side faces 28 and 30, FIG. 2, and upper and lower faces 32, 34, FIG. 3. The ram face 26 preferably is tapered at an angle of thirty to thirty-five degrees and is machined into the distal region 18 until the cone reaches top boundary 27, FIG. 2, and side boundary 29, FIG. 3. Alternatively, faces 28, 30, 32 and 34 are planar.

When a replacement ligament has a bone plug to be secured by an interference screw within a bone tunnel, the punch body 12 preferably includes a ridge 40 having a leading distal ramp with a ram surface 42 for compacting the bone to provide a channel for the interference screw. The distal ram surface 42 preferably has a taper of approximately thirty degrees.

Upper guide surface 24 carries depth markings 50 which correspond to lines 52 on ridge surface 44. The depth markings 50 are in millimeters to indicate the depth of insertion of planar guide faces 21 into the tunnel; intersection 54 between the full cross-sectional dimensions of guide faces 21 and the tapered ram face 28 and 30 corresponds to the "zero" mark. The markings 50, 52 are viewable during surgery using an arthroscope.

For use with a bone plug having a width of no more than 0.335 inch, the punch body 12 has a width of 0.355 inch (9 mm), a height of 0.24 inch and a length for guide faces 21 of 30 mm. The ridge 40 has a height of 0.12 inch, a width of 0.16 inch, a length for ram surface 42 of approximately 5 mm, and a length for upper surface 44 of approximately 20 mm (0.80 inch). The punch body 12 defines a socket 60, shown in phantom, in proximal region 20. The socket 60 has a length of 0.45 inch, and a height of 0.157 inch. The punch 10 preferably is constructed of an alloy of stainless steel such as 17-4 alloy; the punch body 12, the shaft 14 and the handle 16 are welded together.

Figure 4B:
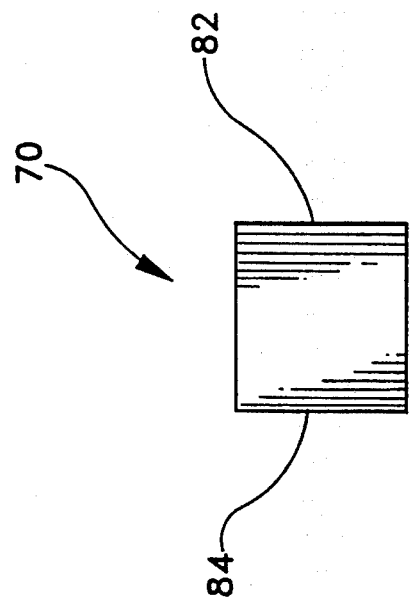
FIG. 4B is an end elevational view of the sizing block of FIG. 4A.
Figure 4A:
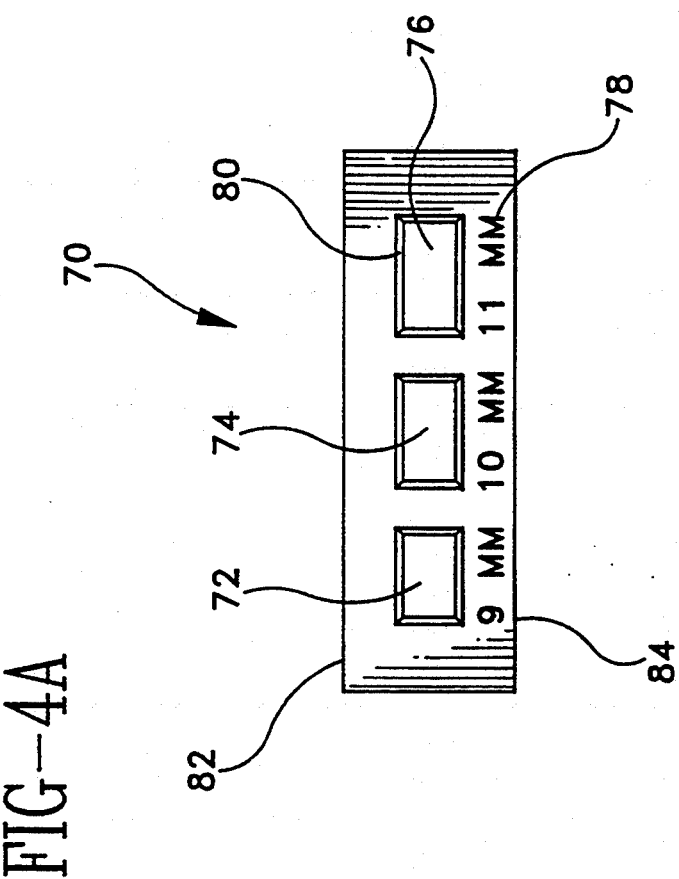
FIG. 4A is a top plan view of a bone plug sizing block according to present invention.

The bone punch 10 preferably is used with a bone plug sizing block 70, FIGS. 4A-4B, defining sizing openings 72, 74 and 76 having a cross-sectional shape substantially the same as the polygonal shape of the bone punch, with dimensions at least slightly smaller than the cross-section of the bone punch. The sizing block 70 includes characters 78 which indicate the width of a bone punch according to this invention to be matched with a bone plug that fits within one of the respective openings. For the dimensions given above with the 9 mm bone punch, the sizing opening 72 has a width of 0.335 inch, and all sizing openings 72, 74, 76 have a height of 0.217 inch. For punch bodies having a width of 0.395 inch (10 mm) and 0.435 inch, (11 mm) the openings 74, 76 have widths of 0.375 inch and 0.415 inch, respectively. The bone plug thereby is selected to have slightly smaller cross-sectional dimensions. Alternatively, a bone punch having a width smaller than that of the bone plug is selected so that the bone plug engages a portion of the bone tunnel wall after insertion.

Each opening 72, 74, 76 is bordered by a chamfered edge 80 which is beveled at a forty-five degree angle. The sides 82, 84 of the sizing block 70 preferably are knurled to provide increased grip for a surgeon or his assistant.

A polygonal bone punch according to the present invention is used as follows during reconstruction of an anterior cruciate ligament. A patellar tendon autograph is harvested from the tibia and kneecap using conventional procedures, such as described in U.S. Pat. No. 5,139,520, incorporated herein by reference. Alternatively, an allograft is obtained from another donor. Circular tunnels are drilled in the tibia and femur.

The bone plug at the femoral end of the graft is sized using a sizing block, and a bone punch according to the present invention having a corresponding polygonal cross-section is selected. The bone punch is inserted through the tibial tunnel after the lower leg is positioned to align the tibial tunnel with the femoral tunnel. Alternatively, a one-inch capsulotomy is made just above the tibial plateau with the knee flexed at approximately 110 degrees, and the bone punch is inserted directly through the soft tissue.

After insertion of the bone punch into the joint, the conical tip of the distal region of the punch body is placed at the opening of the femoral tunnel, and force is applied to the handle and shaft to drive the punch body into the femoral tunnel to alter its cross-sectional shape to match that of the punch body. As described above, the cross-section of the tunnel typically would be converted from circular to rectangular. The depth of insertion is selected according to the length of the bone plug, preferably so that depth equals length; the depth is observed arthroscopically using the depth markings.

The conical ram face 26 of the 9 mm punch body 12 compacts a tunnel having a drilled diameter of 0.315 inch (8 mm) into a rectangular cross-section having a height of 0.24 inch and a width of 0.355 inch as described above. It is desirable to use a drill bit approximately one mm smaller than the width of the punch body. The guide faces 21 serve to maintain a single axis of insertion along the axis of the bone tunnel. After 5 mm of insertion of the full-cross-section, the ram surface 42 begins to force a screw insertion channel into the tunnel's cross-section. After 10 mm of insertion, the upper surface 44 of ridge 40 further serves to guide and stabilize insertion of the punch body 12.

Additionally, a visual or tactile indication can be provided on the shaft or the handle to show the orientation of the guide faces or of the ridge relative to the shaft or handle. For example, the handle can be elongated along a plane aligned with the height of the ridge.

Although specific features of the invention are shown in some drawings and not in others, this is for convenience only as each feature may be combined with any or all of the other features in accordance with the invention.

Other embodiments will occur to those skilled in the art and are within the following claims.

What is claimed is:

1. A bone punch for altering the cross-sectional shape of a tunnel formed in bone, the punch comprising:
    a punch body having a distal region, a proximal region, and a plurality of planar guide faces extending between said distal and proximal regions to define a polygon in cross-section;
    a ridge having a distal portion and a proximal portion and extending along one of said guide faces for providing a channel for an interference screw;
    said distal region terminating in a narrowed leading end; and
    a shaft, connected to said proximal region, through which force is transmittable to drive said punch body into the bone tunnel to alter the cross-sectional shape of the bone tunnel to match the polygonal cross-section of said punch body.

2. The punch of claim 1 wherein said punch body has a longitudinal axis and said guide faces extend substantially parallel to said longitudinal axis.

3. The punch of claim 1 wherein said guide faces have a length of at least 20 mm.

4. The punch of claim 1 wherein said leading end of said distal region defines at least one tapered ram face for engaging a corresponding area of the bone tunnel to compact the bone.

5. The punch of claim 1 wherein said distal portion of said ridge defines a ramp having a distal ram surface for compacting the bone to provide the screw channel.

6. A bone punch for altering the cross-sectional shape of a tunnel formed in a femur, the punch comprising:
    a punch body having a distal region, a proximal region and a plurality of planar guide faces extending between said distal and proximal regions to define a polygon in cross-section, said punch body having a longitudinal axis and said guide faces extending substantially parallel to said longitudinal axis;
    said distal region terminating in a narrowed leading end which defines a conical ram face for engaging a corresponding area of the bone tunnel to compact the bone; and
    a shaft, connected to said proximal regions, through which force is transmitted for driving said punch body into the bone tunnel to alter the cross-sectional shape of the bone tunnel to match the polygonal cross-section of said punch body.

7. The punch of claim 6 wherein the polygonal cross-section of said punch body is rectangular.

8. The punch of claim 7 further including a ridge having a distal portion and a proximal portion and extending along one of said guide faces for providing a channel for an interference screw.

9. The punch of claim 8 wherein said distal portion of said ridge defines a ramp having a distal ram surface for compacting the bone to provide the screw channel.

10. The punch of claim 9 wherein at least one of said guide faces and said ridge carry markings to indicate depth of insertion of said punch body into the femoral tunnel.

11. A combination of a bone punch and a bone plug sizing block, the combination comprising:
    a bone punch for altering the cross-sectional shape of a tunnel formed in bone, the punch including:
        a punch body having a distal region, a proximal region and a plurality of planar guide faces extending between said distal and proximal regions to define a polygon in cross-section, said punch body having a longitudinal axis and said guide faces extend substantially parallel to said longitudinal axis;
        a ridge having a distal portion and a proximal portion and extending along one of said guide faces for providing a channel for an interference screw;
        said distal region terminating in a narrowed leading end which defines at least one tapered ram face for engaging a corresponding area of the bone tunnel to compact the bone; and
        a shaft, connected to said proximal region, through which force is transmitted to drive said punch body into the bone tunnel to alter the cross-sectional shape of the bone tunnel to match the polygonal cross-section of said punch body; and
    a sizing block defining a sizing opening through which a bone plug is insertable and having a cross-sectional shape substantially the same as said polygonal shape of said bone punch.

12. The combination of claim 11 wherein said sizing opening has dimensions at least slightly smaller than said cross-section of said bone punch, and the polygonal cross-section of said punch body is rectangular.

13. The combination of claim 12 wherein said distal portion of said ridge defines a ramp having a distal ram surface for compacting the bone to provide the screw channel.

14. The combination of claim 13 wherein at least one of said guide faces and said ridge carry markings to indicate depth of insertion of said punch body into the bone tunnel, and said sizing block defines characters indicating a width of a bone punch to be matched with a bone plug having a width at least as small as the width of said sizing opening.

* * * * *